(12) United States Patent
Grayson et al.

(10) Patent No.: US 10,444,187 B2
(45) Date of Patent: Oct. 15, 2019

(54) SYSTEM AND METHOD FOR ELECTRICAL CHARACTERIZATION OF ELECTRICAL MATERIALS

(71) Applicant: Northwestern University, Evanston, IL (US)

(72) Inventors: Matthew Grayson, Evanston, IL (US); Jiajun Luo, Evanston, IL (US)

(73) Assignee: Northwestern University, Evanston, IL (US)

( * ) Notice: Subject to any disclaimer, the term of this patent is extended or adjusted under 35 U.S.C. 154(b) by 239 days.

(21) Appl. No.: 15/690,624

(22) Filed: Aug. 30, 2017

(65) Prior Publication Data

US 2018/0188205 A1    Jul. 5, 2018

Related U.S. Application Data

(60) Provisional application No. 62/381,393, filed on Aug. 30, 2016.

(51) Int. Cl.

| | |
|---|---|
| *G01N 27/72* | (2006.01) |
| *G01R 19/08* | (2006.01) |
| *H05K 1/11* | (2006.01) |
| *G01R 15/20* | (2006.01) |
| *G01R 31/26* | (2014.01) |

(52) U.S. Cl.
CPC ........... *G01N 27/72* (2013.01); *G01R 15/202* (2013.01); *G01R 19/08* (2013.01); *G01R 31/2648* (2013.01); *H05K 1/11* (2013.01); *H05K 2201/032* (2013.01)

(58) Field of Classification Search
CPC .. G01N 27/72; G01R 31/2648; G01R 15/202; G01R 19/08; H05K 1/11; H05K 2201/032
See application file for complete search history.

(56) References Cited

U.S. PATENT DOCUMENTS

| | | |
|---|---|---|
| 3,546,578 A | 12/1970 | Sisson et al. |
| 5,150,042 A | 9/1992 | Look et al. |
| 9,041,389 B2 | 5/2015 | Gokmen et al. |
| 2005/0151552 A1* | 7/2005 | Abraham ........... G01R 31/2648 324/754.03 |
| 2013/0082694 A1 | 4/2013 | Lin et al. |

OTHER PUBLICATIONS

Gerber, Hall Effect Spintronics, School of Physics and Astronomy, Tel Aviv University, Tel Aviv, Israel, 2008 (Year: 2008).*

(Continued)

*Primary Examiner* — Daniel R Miller
(74) *Attorney, Agent, or Firm* — Benesch, Friedlander, Coplan & Aronoff LLP

(57) ABSTRACT

Systems and methods can provide a fast and accurate way to measure conductivity and Hall effect, such that transient conductivities, transient carrier densities or transient mobilities can be measured on millisecond time scales, for example. The systems and methods can also reduce the minimum magnetic field needed to extract carrier density or mobility of a given sample, and reduce the minimum mobility that can be measured with a given magnetic field.

16 Claims, 3 Drawing Sheets

(56) References Cited

OTHER PUBLICATIONS

G. T. Kim, J. G. Park, Y. W. Park, C. Muller-Schwanneke, M. Wagenhals, and S. Roth, "Nonswitching van der Pauw technique using two different modulating frequencies", Review of Scientific Instruments, 70, 2177 (1999).
O. Riss, E Shaked, M. Karpovsky, and A. Gerber, "Offset reduction in Hall effect measurements using a nonswitching van der Pauw technique", Review of Scientific Instruments, 79, 073901 (2008).
H. Rzewuski, Z. Werner, "Differential method for Hall-coefficient measurements in an ac magnetic field", Electronics Letters, 1, 86, (1965).
J. C. Male, "Hall effect measurement in semiconducting chalcogenide glasses and liquids", British Journal of Applied Physics, 18, 1543, (1967).
J. Lindemuth and S.-I. Mizuta, "Hall measurements on low-mobility materials and high resistivity materials", Proc. SPIE 8110, Thin Film Solar Technology III, 811001(2011).
Oki Gunawan, Yudistira Virgus, and Kong Fai Tai, "A parallel dipole line System", Applied Physics Letters, 106, 062407.

* cited by examiner

SYSTEM AND METHOD FOR ELECTRICAL CHARACTERIZATION OF ELECTRICAL MATERIALS

CROSS-REFERENCE TO RELATED APPLICATIONS

This patent application claims the benefit of U.S. Provisional Patent Application No. 62/381,393, filed Aug. 30, 2016, the entire contents of which are incorporated by reference herein in their entirety.

STATEMENT OF FEDERALLY FUNDED RESEARCH OR SPONSORSHIP

This invention was made with government support under FA9550-15-1-0247 awarded by the Air Force Office of Scientific Research and DMR1121262 awarded by the National Science Foundation. The government has certain rights in the invention.

BACKGROUND

Conductivity, mobility and carrier density can be important parameters for characterization of electronic materials. Yet accurate measurements of materials can be difficult to achieve with standard methods. Firstly, time varying carrier density or mobility cannot be accurately characterized because multiple sequential measurements with different contact configurations are typically required. Time varying carrier density is known to occur in amorphous oxide semiconductors which are driving today's flat-panel industry, and proper characterization of such carrier density transients could help to identify and eliminate their detrimental effects. Secondly, low mobility materials can require unreasonably large magnetic fields to characterize using traditional Hall effect methods. Thirdly, low mobility materials tend to mix the Hall effect signal with a large, drifting background offset, making accurate measurements difficult. Low-mobility materials include conducting oxides for display front-plane interconnects and organic conductors for flexible electronics.

A traditional method of Hall measurement is to measure a pair of Hall resistances $R_H^+$ in a positive magnetic field and $R_H^-$ in a negative magnetic field sequentially and calculate $R_H^+ - R_H^-$ to obtain the Hall resistance. This requires switching magnetic field polarity. Alternately, one can switch measurement contacts either manually or electrically. There is a prior non-switching van der Pauw technique that measures $R_H^+$ and $R_H^-$ simultaneously, but each component still has a large offset, which introduces large measurement error for low mobility materials. An AC field method reduces noise from the large offset by modulating the magnetic field with a fixed frequency and measuring only at the desired frequency. However, the AC magnetic field can require a complex control unit including a mechanical motor to physically rotate the magnet or a precisely controlled electromagnet, taking a long time to conduct one measurement, and has limited maximum field strength. The AC field method is also incompatible with the non-switching van der Pauw technique, so in principle two sequential AC magnetic field sample configurations would need to be measured.

DESCRIPTION

The systems and methods can measure conductivity, carrier density, and carrier mobility of an electrical conductor. In some examples, the systems and methods provide sensitivity at moderate magnetic fields. By measuring a single output voltage with appropriate four-point configuration of current and voltage contacts, carrier density can be accurately determined. Other numbers of points can be used. For Hall effect, the Hall signal can be measured with a single polarity of magnetic field, whereas previously, multiple measurements were needed, either with alternative contact configurations or at opposite magnetic fields. The system and method can also cancel all parasitic signals, e.g., background offset in Hall measurements, thus the carrier density and mobility of low mobility materials, including but not limited to amorphous oxides, ionic conductors and organic semiconductors, can be extracted with significantly improved accuracy.

The described heterodyne four-point characterization system and method can allow two simultaneous measurements to be combined at once, making it possible to extract carrier density (or Hall resistance) in a single measurement, without the need for sequential measurements as required using standard methods. As a result, the system and method can be faster than standard methods and can characterize time-dependent transients. The system and method can also demonstrate enhanced sensitivity over prior methods for accurate measure of Hall effect at significantly smaller magnetic fields than required for standard circuits.

Figure 1A:
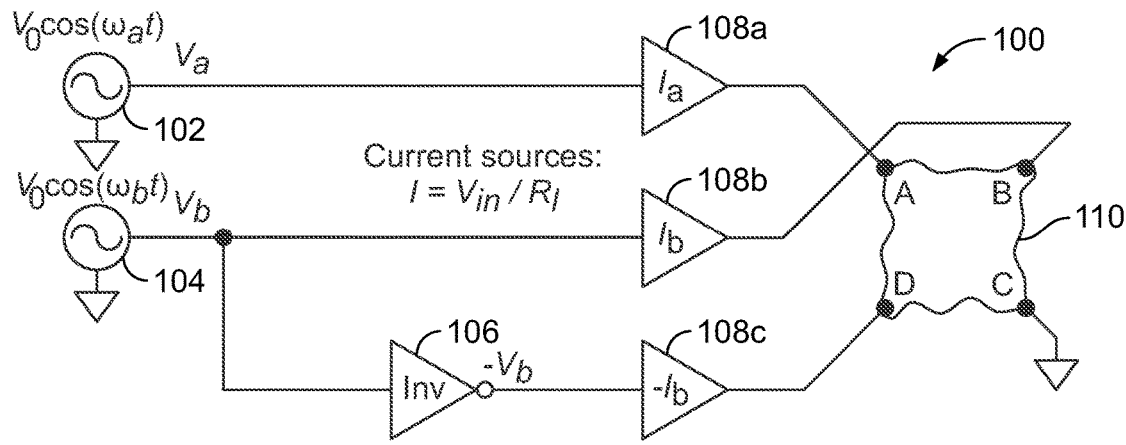
FIGS. 1A and 1B are example current source and voltage heterodyne circuits of a heterodyne Hall process which can characterize a sample of electronic material via contacts A, B, C, and D.
Figure 1B:
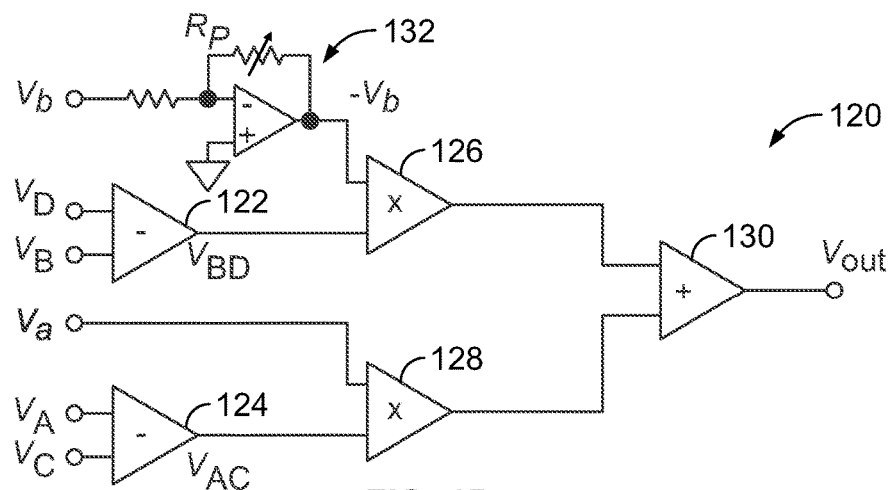

FIGS. 1A-1B are an example current source circuit 100 and voltage heterodyne circuit 120 for a heterodyne Hall process, e.g., for fast and accurate magnetotransport characterization of electrical material 110, e.g., semiconductors, transparent metals, including but not limited to, the conducting back-planes of flat-panel displays, etc. The characterization can help optimize, for example, that the composition and fabrication processes used create materials with determined mobility. FIG. 1A shows components of circuit 100 that can provide driving current. FIG. 1B shows components of circuit 120 that combine voltages at the contacts A, B, C, D of the material 110 to yield a single output voltage $V_{out}$. Four contacts are shown, but other numbers of contacts can be used. The conductivity process can determine a conductivity of the material 110, which can include the product of a carrier density n and mobility μ of the material 110. The Hall process can separately determine a conducting material's carrier density n and, in conjunction with the conductivity measurement, its mobility μ.

In FIG. 1A, the traditional Hall effect can provide a transverse 4-point resistance of the material 110 for measuring at contacts A, B, C, D during a magnetic field B sweep between −B and +B. Since the contacts A, B, C, D cannot be perfectly symmetric, the directly measured transverse resistance $R_{xy}$ can include a longitudinal component $R_{xy,0}$, preventing a complete cancellation of $R_{xy}=0$ when B=0. The $R_{xy,0}$ component can also vary during the B sweep. Thus, an accurate Hall measurement cancels out the error introduced by $R_{xy,0}$. An example process to eliminate this error is to conduct a full B sweep between −B and +B. In a Drude model, the $R_{xy,0}$ component is evenly symmetric with B, $R_{xy,0}(+B)=R_{xy,0}(-B)$, and the transverse component $R_{xy,H}$ is oddly symmetric, $R_H^+ = R_{xy,H}(+B) = -R_{xy,H}(+B) = -R_H^-$. Thus, the pure transverse resistance $R_{xy,H}$ can be obtained from the difference between $R_{xy}$ measured at positive and negative B field, as Eq. (1).

$$R_{xy}(+B) - R_{xy}(-B) = [R_{xy,0}(+B) + R_{xy,H}(+B)] - [R_{xy,0}(-B) + R_{xy,H}(-B)]$$
$$= [R_{xy,0}(+B) - R_{xy,H}(-B)] + [R_{xy,0}(+B) - R_{xy,H}(-B)]$$
$$= R_H^+ - R_H^- \quad (1)$$

The circuit 100 can include a first voltage source 102 which outputs voltage signal $V_a$ and a second voltage source 104 which outputs voltage signal $V_b$. In some examples, the first voltage source 102 and/or second voltage source 104 are alternating current voltage sources. The voltage signal $V_b$ can be split into two signals and one of the split signals can be input to an inverter 106 to provide voltage signal $-V_b$. The voltages $V_a$, $V_b$ and $-V_b$ can be converted into currents $I_a$, $I_b$ and $-I_b$, e.g., via current sources 108a-c. The current sources 108a-c convert input voltages to currents with the ratio determined by resistance $R_I$. The outputted currents $I_a$, $I_b$ and $-I_b$ can connect with contact points A, B, C or D of material 110. In some examples, current $I_a$ can connect with contact A, current $I_b$ can connect with contact B, and current $-I_b$ can connect with contact D. Contact C can connect with ground.

When applied in a Hall effect measurement in novel electrical materials of interest, two problems can prevent the traditional Hall measurement process from obtaining accurate results. Firstly, the electrical properties of materials of interest such as amorphous oxide thin films constantly change in time due to photoresponse. During a Hall measurement, the magnetic sweep between positive and negative B field can take a long time as the sweeping rate of B is limited. Only the average electron density n, and therefore mobility μ, can be measured during the sweep. Moreover, in addition to having a magnetic field dependence, the longitudinal resistance component $R_{xy,0}$ can also vary over time due to temperature variation, introducing extra measurement error. Indeed, increased variance in the Hall mobility μ can be observed immediately after switching the state of a light emitting diode (LED), when conductivity σ is changing rapidly.

Secondly, materials of interest such as amorphous materials and ionic conductors still have mobility μ much lower than that of crystalline Si. This leads to a much lower signal-to-noise ratio (SNR) in their Hall measurements. In a Hall measurement, the desired signal is the $R_{xy,H}$ component, and the noise comes mainly from the $R_{xy,0}$ component. Therefore, SNR is proportional to the product of μ and B.

$$SNR \propto \frac{R_{xy,H}}{R_{xy,0}} \propto \frac{B/ned}{1/ne\mu d} = \mu B \quad (2)$$

For low mobility materials including amorphous materials, e.g., IGZO, a magnetic sweep to above 1 T is normally required for an accurate Hall measurement. Such a large required magnetic field further increases the sweeping time and may introduce extra error.

Following the Onsager-Casimir relation, the measured 4-point resistance is invariant if the exchange of current and voltage contacts is accompanied by a magnetic field reversal. This implies that $R_{xy}(+B)=R_{AC,BD}(+B)=R_{BD,AC}(-B)$ and $R_{xy}(-B)=R_{AC,BD}(-B)=R_{BD,AC}(+B)$. Thus, instead of a sweep between positive and negative B fields, one only needs to sweep between 0 and the positive field. Using the non-switching technique, both $R_{xy}(+B)$ and $R_{xy}(-B)$ can be measured simultaneously during the positive field sweep, doubling the measurement efficiency. To achieve increased accuracy for low mobility materials, the $R_{xy,H}$ component is separated from the $R_{xy,0}$ component. The AC magnetic field, which modulates field B thus $R_{xy,H}$ with a low frequency, can be used to get higher SNR in low mobility Hall measurements. However, modulating the B field itself can require a complex magnet system design with a mechanical motor or a modulated electromagnet, and also significantly longer measurement duration.

The heterodyne Hall process of FIGS. 1A and 1B uses the circuit 100 and 120 to cancel background offset $R_{xy,0}$ and measures just the Hall resistance component $R_{xy,H}$ (B) directly. With the circuits 100 and 120, Hall measurements can take much less time and have a higher SNR.

The circuit 100 generates the excitation currents $I_a$, $I_b$, $-I_b$ and connects them to four contacts A, B, C, D, e.g., using the van der Pauw configuration. The circuit 120 uses the voltage at the four contacts A, B, C, D to generate a single output voltage $V_{out}$ to realize a heterodyne Hall effect method. The two AC voltage sources 102, 104, generating $V_a$ and $V_b$, operating at different frequencies, $\omega_a$ and $\omega_b$, and the same amplitude, $V_0$, can be used as power sources. In some cases, the two voltage sources can have different amplitudes.

$$V_a(t)=V_0 \cos(\omega_a t+\theta_a)$$

$$V_b(t)=V_0 \cos(\omega_b t+\theta_b) \quad (3)$$

The AC voltages $V_a$ and $V_b$ are sent to current sources 108a-c with resistance $R_I$, to generate input currents $I_a$ and $I_b$ as following, where $I_0=V_0/R_I$.

$$I_a(t)=I_0 \cos(\omega_a t+\theta_a)$$

$$I_b(t)=I_0 \cos(\omega_b t+\theta_b) \quad (4)$$

The four contacts A, B, C, D, arranged using the van der Pauw configuration, are connected to the circuit 120. Current $I_a$ is supplied from contact A to contact C, and current $I_b$ is supplied from contact B to contact D. In the example shown in FIGS. 1A and 1B, contact C is fixed to be the ground contact. Thus two current sources 108b-c driven by opposite driving voltages $V_b$ and $-V_b$ are used to provide a constant current $I_b$ through the sample while also allowing contacts B and D to be at any voltage.

The transverse voltage $V_{BD}$ and $V_{AC}$, provided by analog subtractors 122 and 124 respectively, during Hall measurement is therefore determined by Eq. (5), where $Z_{BD}$ and $Z_{AC}$ are the two-point impedances across contacts BD and AC respectively. They include contributions from both the sample and the contacts A, B, C, D, and may have capacitive components when the contacts are not perfectly ohmic. In the heterodyne Hall process, details of the compositions in $Z_{BD}$ and $Z_{AC}$ are irrelevant, as long as they remain constant.

$$V_{BD}(t)=I_0[R_{xy}(+B)\cos(\omega_a t+\theta_a)+Z_{BD}\cos(\omega_b t+\theta_b)]$$

$$V_{AC}(t)=I_0[R_{xy}(-B)\cos(\omega_b t+\theta_b)+Z_{AC}\cos(\omega_a t+\theta_a)] \quad (5)$$

The transverse voltage $V_{BD}$ is modulated at frequency $\omega_b$ by multiplying with $-V_b$, and $V_{AC}$ is modulated at frequency $\omega_a$ by multiplying with $V_a$, via analog multipliers 126 and 128, respectively. The modulated signals are added together at adder 130 to produce a single output voltage $V_{out}$ in FIG. 1, as given in Eq. (6), where $V_R$ is the reference voltage used in the multipliers.

$$V_{out} = \frac{V_{AC}(t)V_a(t) - V_{BD}(t)V_b(t)}{V_R}$$
$$= \frac{-V_0^2}{2V_R R_I}\begin{Bmatrix} (R_B^+ - R_H^-)\cos[(\omega_a+\omega_b)t + (\theta_a+\theta_b)] + \\ (R_H^+ - R_H^-)\cos[(\omega_a-\omega_b)t + (\theta_a-\theta_b)] + \\ \text{Re}(Z_{BD})\cos[2(\omega_b t+\theta_b)] - \text{Im}(Z_{BD})\sin[2(\omega_b t+\theta_b)] - \\ \text{Re}(Z_{AC})\cos[2(\omega_a t+\theta_a)] + \text{Im}(Z_{AC})\sin[2(\omega_a t+\theta_a)] + \\ \text{Re}(Z_{BD}) - \text{Re}(Z_{AC}) \end{Bmatrix} \quad (6)$$

The output signal has 5 frequency components. The value of interest $R_H^+ - R_H^-$ appears at frequency $\omega_a+\omega_b$ and $\omega_a-\omega_b$. All other signals are separated to different frequencies. Thus, only the voltage amplitude at either frequency $\omega_a+\omega_b$ or $\omega_a-\omega_b$ is needed to know $R_H^+ - R_H^-$. For example, the root-mean-square (RMS) voltage at frequency $\omega_a+\omega_b$ of $V_{out}$ is measured and determined as $V_{hetero}$. Carrier density n is related to $V_{hetero}$ through Eq. (7).

$$V_{hetero} = -\frac{V_{out,\omega_a+\omega_b}}{\sqrt{2}} = -\frac{V_0^2}{2\sqrt{2}V_R R_I}[2R_{xy,H}(+B)] = -\frac{V_0^2}{\sqrt{2}V_R R_I}\cdot\frac{B}{ned} \quad (7)$$

Mobility $\mu$ can be calculated from carrier density n when the sheet resistance $R_{sheet}$ is also known. To verify the heterodyne Hall process, an example circuit has been built and tested on a 200 nm thick amorphous-InGaZnO (a-IGZO) thin film sample grown by pulsed laser deposition (PLD) with ambient oxygen pressure of 5 mTorr with steady electrical properties. The sample has sheet resistance $R_{sheet}$=11.7 kΩ, as measured using the van der Pauw method.

Figure 2:
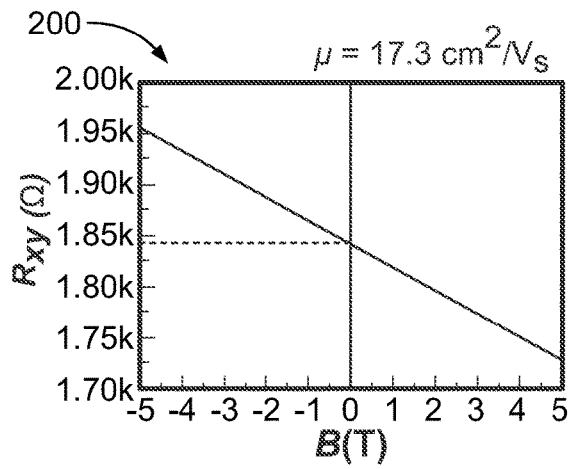
FIG. 2 is a graph of example measurement results of $R_{xy}$ using standard Hall process on the 200 nm thick pulsed-laser deposited amorphous-In—Ga—Zn—O test sample grown, for example, under P=5 mTorr oxygen ambient pressure.

FIG. 2 is a graph 200 of example measurement results of $R_{xy}$ using standard Hall process on the 200 nm 5 mTorr PLD-grown a-IGZO test sample. FIG. 2 shows example results when measured using the standard 4-point Hall process, with magnetic field B sweeping between −5 T to 5 T. From the $R_{xy}$ slope, it is determined that n=1.55×10$^{18}$ cm$^{-3}$ and μ=17.3 cm$^2$/Vs. In the measured $R_{xy}$ results, background offset is $R_{xy,0}$=1.84 kΩ and the response $R_{xy,H}$/B is only 20 Ω/T.

Figure 3A:
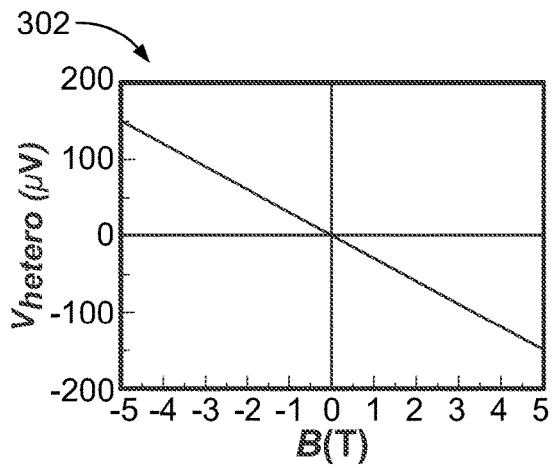
FIGS. 3A and 3B are graphs of example magnetic field sweep results using the heterodyne Hall process on low mobility materials.
Figure 3B:
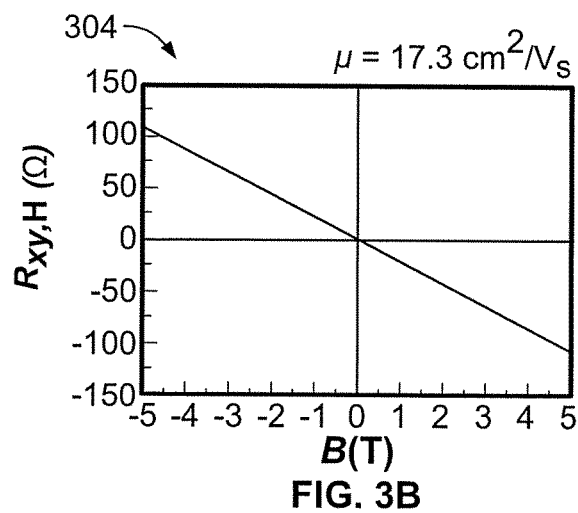

FIGS. 3A and 3B are graphs 302, 304 of example magnetic field sweep results using the heterodyne Hall process on low mobility materials, e.g., an example 200 nm 5 mTorr PLD-grown a-IGZO test sample. When applying the heterodyne Hall process, the a-IGZO sample can be used and along with $V_0$=√2 V, $V_R$=10 V, and $R_I$=100 kΩ. With $\omega_a$=1.7 Hz and $\omega_b$=6.8 Hz, an example measured voltage $V_{hetero}$ is plotted in FIG. 3A, and the calculated Hall resistance $R_{xy,H}$ in FIG. 3B. In the heterodyne Hall process, $R_{xy,H}$ is directly measured and the background offset equals to 0.

Because there is no background offset in the heterodyne Hall process results, the $V_{hetero}$/B slope, and thus the $R_{xy,H}$/B slope can be directly identified from a single data point at any sufficiently large B field, as long as the $V_{hetero}$ signal is sufficiently larger than measurement noise. Using the output value at B=4 T in FIG. 3A, in one example, the calculated carrier density n is 1.54×10$^{18}$ cm$^{-3}$ and the sample mobility μ is 17.3 cm$^2$/Vs, both agree well with that obtained from a complete magnet sweep.

Figure 4:
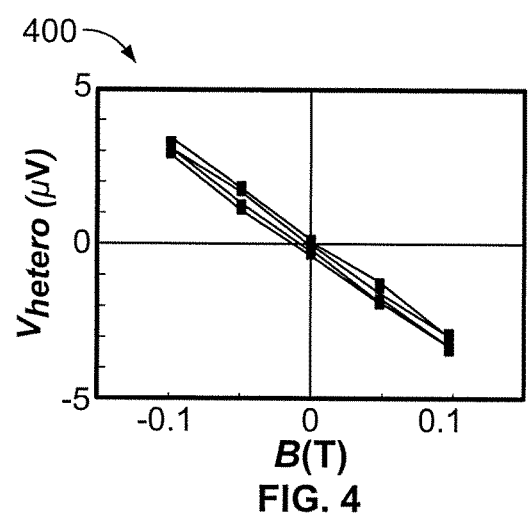
FIG. 4 is a graph of an example measurement result of using the heterodyne Hall process at low magnetic field.

In the cases where only small magnet fields are available, a more accurate Hall measurement is possible by flipping the magnetic field. FIG. 4 is a graph 400 of an example a measurement result of $V_{hetero}$ using the heterodyne Hall process on low mobility materials, e.g., an example 200 nm 5 mTorr PLD-grown a-IGZO test sample. This two-field method has been tested on the test a-IGZO sample with B=+0.1 T. $V_{hetero}$ results are shown in FIG. 4. The measurement of $V_{hetero}$ can be repeated several times to check reproducibility of the results. From the voltage difference at B=−0.1 T and B=0.1 T, the calculated carrier density n is 1.50×10$^{18}$ cm$^{-3}$ and the sample mobility is 17.8 cm$^2$/Vs. Both are very close to those measured with much large magnetic field.

By canceling the offset signal in Hall measurements, the heterodyne Hall process provides an easy way to measure other low mobility material systems. Estimating from FIG. 4, using electrical components with higher accuracy, the smallest field to extract a slope is $B_{min}$=0.01 T. For samples with different mobility μ, Eq. (2) shows that the minimum measurable μB is a constant that sets the sensitivity of the example, which equals to $\mu B_{min}$=(15 cm$^2$/Vs)×(0.01 T)= (0.0015 m$^2$/Vs)×(0.01 T)=1.5×10$^{-5}$.

As an example of the typical measurement sensitivity, using a 15 T magnet, the minimum measurable mobility is $\mu_{min}$=$\mu B_{min}/B_{typ}$=(15 cm$^2$/Vs)×(0.01 T/15 T)≈0.01 cm$^2$/Vs. As an example of the minimum possible measurable mobility, using the 45 T DC magnetic field at the National High Magnetic Field Lab (HMFL) in Tallahassee, the minimum mobility can reach $\mu_{min,HMFL}$=$\mu B_{min}/B_{HMFL}$=(15 cm$^2$/Vs)× (0.01 T/45 T)≈0.003 cm$^2$/Vs. Measuring such a low mobility can be important for materials like p-type amorphous delafossite CuAlO$_2$, which has μ=0.03 cm$^2$/Vs, and ionic conductors such as RbAg$_4$I$_5$, which has μ=0.05 cm$^2$/Vs.

Figure 5:
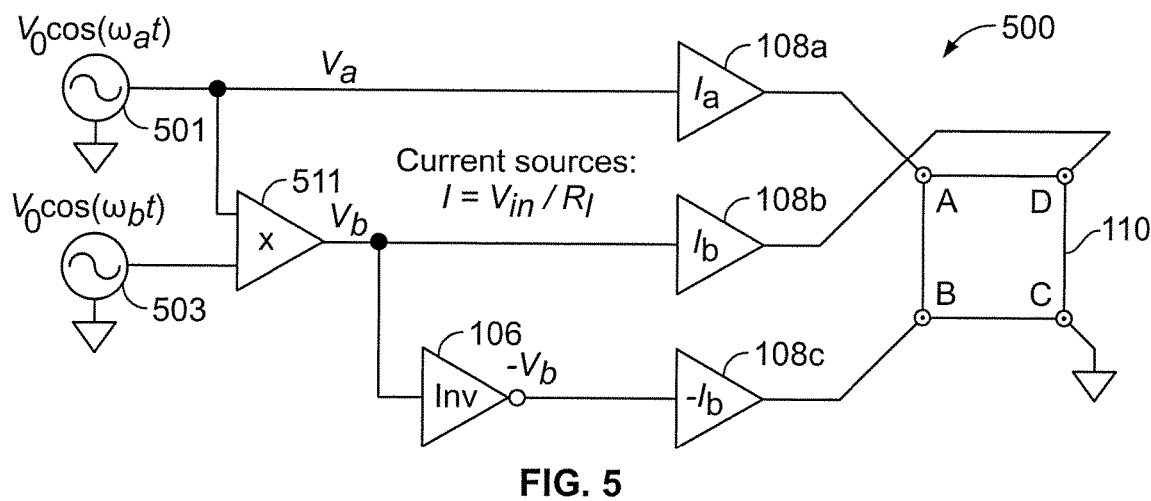
FIG. 5 is another example of a current source circuit of the heterodyne Hall process.

To eliminate possible phase drift, the heterodyne Hall measurement circuit can also be implemented using driving voltages where $V_b$ is a mix of signals at frequencies $\omega_a$, and $\omega_b$. As an example, FIG. 5 shows a possible current source circuit 500, where $V_a$ is connected with a sine voltage source 501 operating at frequency $\omega_a$, and $V_b$ is the output of multiplier 511 with sine wave inputs 501 and 503 at different frequencies $\omega_a$ and $\omega_b$, and the same amplitude $V_0$. In the example of circuit 500, the input voltages $V_a$ and $V_b$ are given by Equation (8), where $V_R$ is the reference voltage for multiplier 511. In some cases, it may be advantageous to use different amplitudes for voltage sources 501 and 503.

$$V_a(t)=V_0\cos(\omega_a t+\theta_a)$$

$$V_b(t)=V_0^2\cos(\omega_a t+\theta_a)\cos(\omega_b t+\theta_b)/V_R \quad (8)$$

Using the same voltage heterodyne circuit 120 as in FIG. 1B. The Hall effect signal of interest can be measured at the output with frequency $\omega_b$:

$$V_{out,\omega_b} = -\frac{V_0^3}{2V_R^2 R_I}(R_H^+ - R_H^-)\cos(\omega_b t + \theta_b) \quad (9)$$

All other signals are separated to different frequencies. And the directly measurable root-mean-square (RMS) voltage $V_{hetero}$ can be used to calculate the carrier density n through equation (10). The mobility $\mu$ can then be calculated when the sheet resistance $R_{sheet}$ is also known.

$$V_{hetero} = \frac{V_{out,\omega_b}}{\sqrt{2}} = -\frac{V_0^3}{2\sqrt{2} V_R^2 R_I}[2R_{xy,H}(+B)] = -\frac{V_0^3}{\sqrt{2} V_R^2 R_I} \cdot \frac{B}{ned} \quad (10)$$

Figure 6A:
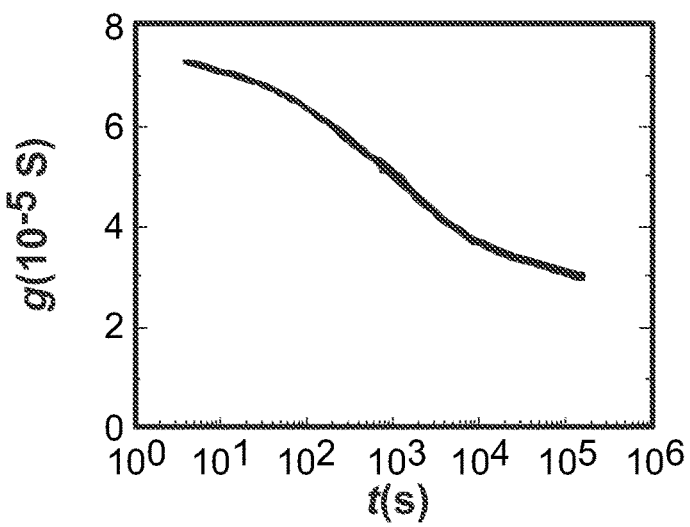
FIG. 6A is a graph of an example conductivity transient in a black phosphorous test sample.
Figure 6B:
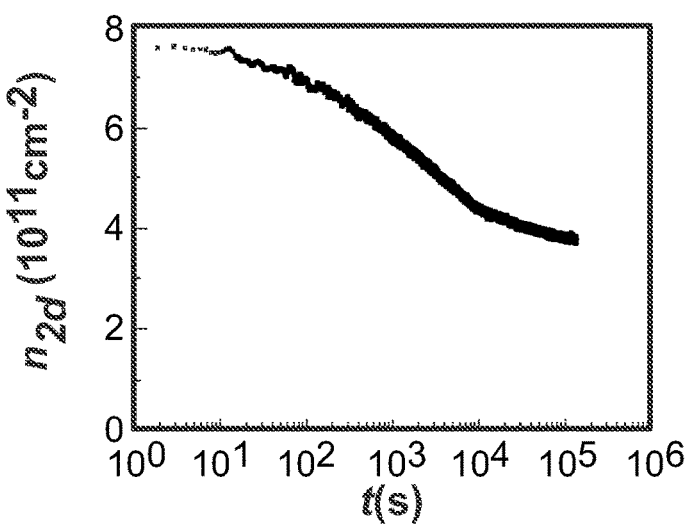
FIG. 6B is a graph of an example of the carrier density transient in the same sample as FIG. 6A using the heterodyne Hall process at a constant magnetic field.
Figure 6C:
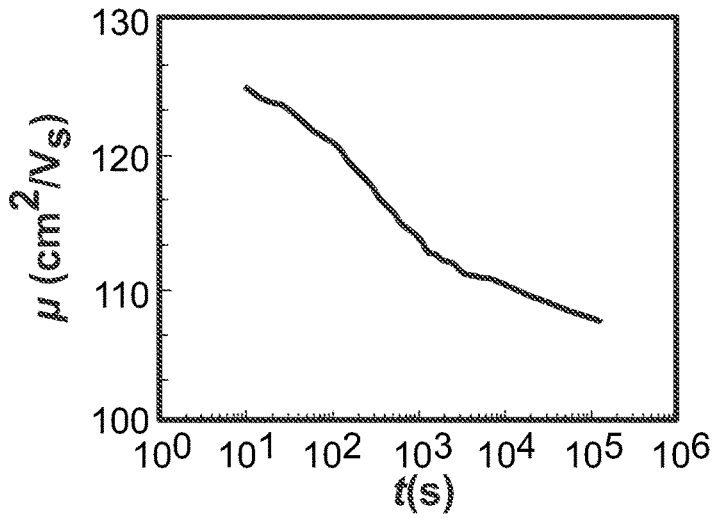
FIG. 6C is an example of a graph of mobility transient calculated from the carrier density transient.

FIG. 6A is a graph of an example conductivity transient in a black phosphorous test sample. FIG. 6B is a graph of an example of the carrier density transient in the same sample as FIG. 6A using the heterodyne Hall process at a constant magnetic field. FIG. 6C is an example of a graph of mobility transient calculated from the carrier density transient. Advantages can include, for Hall effect characterization, a system and method that measures in a single signal at a single polarity of magnetic field the full information of two Hall measurements. Thus, the system and method can speed up Hall measurements since there is no need to switch contacts, allowing rapid transient (10 ms or shorter timescale) Hall effect measurements of arbitrarily shaped samples. FIG. 6A shows an example of the conductivity and FIG. 6B the carrier density transient measured on a black phosphorous test sample using the heterodyne Hall process. The mobility transient can therefore be calculated from the carrier density and sheet resistance transient, as shown in FIG. 6C.

Advantages can also include, for Hall effect, a system and method that eliminates the zero-filed offset and measures the pure Hall effect resistance. As a result, the system and method can allow Hall measurements with significantly lower magnetic field and higher sensitivity.

The systems and methods can provide faster and more accurate measurement of carrier density and mobility in electrical materials. The system and method can be adapted in scientific instruments. The systems and method can allow characterization of electrical materials with mobilities lower than that can be measured with existing technologies. The systems and methods may be implemented in many different ways in many different combinations of hardware, software firmware, or any combination thereof. In one example, the systems and methods can be implemented with a processor and a memory, where the memory stores instructions, which when executed by the processor, causes the processor to perform the systems and methods. The processor may mean any type of circuit such as, but not limited to, a microprocessor, a microcontroller, a graphics processor, a digital signal processor, or another processor. The processor may also be implemented with discrete logic or components, or a combination of other types of analog or digital circuitry, combined on a single integrated circuit or distributed among multiple integrated circuits. All or part of the logic described above may be implemented as instructions for execution by the processor, controller, or other processing device and may be stored in a tangible or non-transitory machine-readable or computer-readable medium such as flash memory, random access memory (RAM) or read only memory (ROM), erasable programmable read only memory (EPROM) or other machine-readable medium such as a compact disc read only memory (CDROM), or magnetic or optical disk. A product, such as a computer program product, may include a storage medium and computer readable instructions stored on the medium, which when executed in an endpoint, computer system, or other device, cause the device to perform operations according to any of the description above. The memory can be implemented with one or more hard drives, and/or one or more drives that handle removable media, such as diskettes, compact disks (CDs), digital video disks (DVDs), flash memory keys, and other removable media.

The processing capability of the system may be distributed among multiple system components, such as among multiple processors and memories, optionally including multiple distributed processing systems. Parameters, databases, and other data structures may be separately stored and managed, may be incorporated into a single memory or database, may be logically and physically organized in many different ways, and may implemented in many ways, including data structures such as linked lists, hash tables, or implicit storage mechanisms. Programs may be parts (e.g., subroutines) of a single program, separate programs, distributed across several memories and processors, or implemented in many different ways, such as in a library, such as a shared library (e.g., a dynamic link library (DLL)). The DLL, for example, may store code that performs any of the system processing described above.

While various embodiments have been described, it can be apparent that many more embodiments and implementations are possible. Accordingly, the embodiments are not to be restricted.

We claim:

1. A circuit, comprising:
   a first contact point, a second contact point, a third contact point and a fourth point contact connected with a material for testing, wherein the material conducts electricity, the first contact point, the second contact point and the third contact point connect with respective first, second and third current contacts, and the fourth contact point connects with ground or a fourth current contact, and wherein the first contact point, the second contact point, the third contact point and the fourth contact point connect with respective voltage contacts;
   wherein at least one of the current contacts is to supply a current at a first non-zero frequency, and wherein the other current contacts are to supply respective currents at a second non-zero frequency different than the first non-zero frequency; and
   a single output voltage point connected via a circuit to the voltage contacts, wherein the circuit is to modulate first and second voltages received from the voltage contacts using the first non-zero frequency and the second non-zero frequency, respectively, and to output a single output voltage signal corresponding to a sum of the modulated first and second voltages at the single output voltage point, wherein the single output voltage signal comprises a frequency component indicative of at least one of a conductivity, a carrier density or a mobility of the material.

2. The circuit of claim 1, further comprising a single polarity of magnetic field configured to measure a Hall signal.

3. The circuit of claim 1, further comprising a magnetic sweep configured to cancel parasitic signals.

4. The circuit of claim 1, where the current contacts and voltage contacts are configured to combine two simultaneous measurements at once to extract at least one of a Hall effect resistance or the carrier density in a single measurement without sequential measurements.

5. The circuit of claim 1, wherein the single output voltage signal further comprises characterizing transients.

6. The circuit of claim 1, wherein the material comprises low mobility materials, including amorphous oxides, ionic conductors, or organic semiconductors.

7. The circuit of claim 1, wherein the mobility is determined at a known magnetic field.

8. The circuit of claim 1, wherein the current contacts and the voltage contacts are arranged in a van der Pauw configuration.

9. A method for testing electrical characteristics of a material, comprising:
  providing a material for testing, where the material conducts electricity;
  electrically connecting with the material at a first point, a second point, a third point and a fourth point, the first point, the second point and the third point connecting with respective first, second and third current contacts, and the fourth point connecting with a fourth current contact or ground, and wherein the first point, the second point, the third point and the fourth point are connected with respective voltage contacts;
  supplying from at least one of the current contacts current at a first non-zero frequency, and supplying from the other current contacts respective currents at a second non-zero frequency different than the first non-zero frequency;
  receiving, by a circuit, first and second voltages from the voltage contacts, the circuit modulating the first and second voltages using the first non-zero frequency and the second non-zero frequency, respectively; and
  summing, by the circuit, the modulated first and second voltages to provide a single output voltage signal comprising a frequency component indicative of at least one of a conductivity, a carrier density or a mobility of the material.

10. The method of claim 9, further comprising measuring a Hall signal using a single polarity of magnetic field.

11. The method of claim 9, further comprising providing a magnetic sweep to cancel parasitic signals.

12. The method of claim 9, further comprising combining two simultaneous measurements at once; and
  extracting at least one of the Hall resistance or the carrier density in a single measurement without sequential measurements.

13. The method of claim 9, further comprising characterizing transients from the single output voltage signal.

14. The method of claim 9, wherein the material comprises low mobility materials including amorphous oxides, ionic conductors, or organic semiconductors.

15. The method of claim 9, further comprising determining the mobility at a known magnetic field.

16. The method of claim 9, further comprising arranging the current contacts and the voltage contacts in a van der Pauw configuration.

* * * * *